US007857894B2

(12) United States Patent
Taylor et al.

(10) Patent No.: US 7,857,894 B2
(45) Date of Patent: Dec. 28, 2010

(54) ADSORBENT BED PRESSURE BALANCING FOR A GAS CONCENTRATOR

(75) Inventors: Brenton Taylor, Kenwood, CA (US); Peter Hansen, Santa Barbara, CA (US)

(73) Assignee: Inogen, Inc., Goleta, CA (US)

(*) Notice: Subject to any disclaimer, the term of this patent is extended or adjusted under 35 U.S.C. 154(b) by 225 days.

(21) Appl. No.: 11/973,666

(22) Filed: Oct. 9, 2007

(65) Prior Publication Data

US 2008/0110338 A1 May 15, 2008

Related U.S. Application Data

(60) Provisional application No. 60/851,021, filed on Oct. 10, 2006.

(51) Int. Cl.
*B01D 53/02* (2006.01)

(52) U.S. Cl. .................... 96/113; 95/21; 95/22; 95/96; 95/19; 96/114; 96/121; 128/200.24; 128/205.27; 128/205.28; 128/206.15; 128/207.18

(58) Field of Classification Search .................... 95/19, 95/21, 22, 96; 96/113, 114, 121; 128/200.24, 128/205.27, 205.28, 206.15, 207.18
See application file for complete search history.

(56) References Cited

U.S. PATENT DOCUMENTS

| | | | | |
|---|---|---|---|---|
| 4,693,730 | A | 9/1987 | Miller et al. | |
| 4,807,616 | A * | 2/1989 | Adahan | 128/204.21 |
| 5,092,326 | A * | 3/1992 | Winn et al. | 128/205.13 |
| 5,407,465 | A | 4/1995 | Schaub et al. | |
| 5,529,607 | A | 6/1996 | Tan | |
| 5,661,987 | A * | 9/1997 | Zarate | 62/641 |
| 6,277,174 | B1 | 8/2001 | Neu et al. | |
| 6,471,744 | B1 * | 10/2002 | Hill | 95/19 |
| 6,651,658 | B1 * | 11/2003 | Hill et al. | 128/204.23 |
| 6,837,244 | B2 * | 1/2005 | Yagi et al. | 128/205.11 |
| 7,717,981 | B2 * | 5/2010 | LaBuda et al. | 95/96 |
| 2007/0157931 | A1 * | 7/2007 | Parker et al. | 128/204.23 |

* cited by examiner

*Primary Examiner*—Duane Smith
*Assistant Examiner*—Christopher P Jones
(74) *Attorney, Agent, or Firm*—Mark Rogers

(57) ABSTRACT

A system and a method are described for monitoring pressure imbalances in the adsorbent beds of a portable gas concentrator. Using the programmability features found in modern portable concentrators, various mitigative procedures to adjust for pressure imbalances and to predict the need for service are disclosed.

3 Claims, 5 Drawing Sheets

ADSORBENT BED PRESSURE BALANCING FOR A GAS CONCENTRATOR

RELATED APPLICATIONS

This application claims priority to U.S. Provisional Application Ser. No. 60/851,021, filed Oct. 10, 2006

FEDERALLY SPONSORED RESEARCH

Not Applicable

SEQUENCE LISTING

Not Applicable

BACKGROUND OF THE INVENTION

The invention relates to gas concentrators, and in particular to a concentrator which includes the capability to monitor the pressure of individual adsorbent beds and use the pressure data to track and adjust the concentrator's performance. The application is particularly directed to portable oxygen concentrators for therapeutic use.

The application of oxygen concentrators for therapeutic use is known, and many variants of such devices exist. A particularly useful class of oxygen concentrators is designed to be portable, allowing users to move about and to travel for extended periods of time without the need to carry a supply of stored oxygen. Most of these portable concentrators are based on Pressure Swing Adsorption (PSA) or Vacuum Pressure Swing Adsorption (VPSA) designs which feed compressed air to selective adsorption beds. In a typical oxygen concentrator, the beds selectively adsorb nitrogen, resulting in pressurized, oxygen-rich product gas.

The main elements in an oxygen concentrator are shown in FIG. 1. Air is draw in, and typically filtered, at air inlet 1 before being pressurized by compressor 2. The pressurized air is directed by a valve arrangement through adsorbent beds 3. An exemplary adsorbent bed implementation, used in a concentrator design developed by the inventors, is three columns filled with zeolite powder. The pressurized air is directed through these columns in a series of steps which constitute a PSA cycle. Although many different arrangements of beds are possible as well as a variety of different PSA cycles, the result is that nitrogen is removed by the adsorbent material, and the resulting oxygen rich air is routed to a product gas storage device at 4. Some of the oxygen rich air is routed back through the bed to flush out (purge) the trapped nitrogen to an exhaust. Generally multiple beds, or columns in the exemplary device, are used so at least one bed may be used to make product while at least one other is being purged, ensuring a continuous flow of product gas. The purged gas is exhausted from the concentrator at 6.

Such PSA systems are known in the art, and it is appreciated that the gas flow control through the compressor and the beds in a PSA cycle is complex, and requires precise timing and control of parameters such as pressure and temperature to attain the desired oxygen concentration in the product gas stream. Accordingly, most modern concentrators also have a programmable controller 5, typically a microprocessor, to monitor and control the operation of the PSA cycle and monitor various system parameters to ensure correct device operation. In particular, the controller controls the timing and operation of the various valves used to cycle the beds through feed and purge steps which make up the PSA cycle. Also present in most portable concentrators is a Conserver 7 which acts to ensure that oxygen rich gas is only delivered to a patient when a breath is inhaled, thus using less product than a continuous flow arrangement, thereby allowing for smaller, lighter concentrator design. In the conserver mode, a pulse of oxygen rich air, called a bolus, is delivered in response to a detected breath. A typical concentrator will also contain a user/data interface 8.

A portable oxygen concentrator must be small, light and quiet in order to be useful, while retaining the capacity to produce a flow of product gas, usually a flow rate prescribed by a medical practitioner, adequate to provide for a patient's needs. Although fixed site PSA based concentrators have been available for many years, such fixed site units may weigh 50 pounds or more, be several cubic feet in size and produce sound levels greater than 50 dBA. A portable concentrator on the other hand may weigh on the order of 10 lbs, be less than one half cubic foot in size and produce as little as 35-45 dbA sound levels. The portable concentrators still need to produce the prescribed flow rate of oxygen. Thus portable concentrators involve a significant amount of miniaturization, leading to smaller, more complex designs compared to stationary units. System size, weight and complexity may lead to minimum design margins and tighter manufacturing tolerances to achieve portability.

Therefore it is important that portable concentrator performance is monitored closely, so problems can be compensated for quickly without degrading oxygen service to the patient which could leave patients stranded without an adequate oxygen supply. A key parameter which affects concentrator performance is the balance of the pressure ratio achieved in each bed during the PSA cycle. The purity of the oxygen product depends greatly on the operation of the columns being well balanced in operating parameters; that is, if one column has a slightly longer adsorption step or a higher adsorption pressure ratio or likewise a longer blowdown or countercurrent purge step than the other due to dissimilar valve response times or other tolerance stack-up issues, a significant decrease in product purity will result. Subtle differences in purge step symmetry caused by many different factors other than step timing can also lead to a decrease in product purity if left uncorrected.

Typical home oxygen concentrators are not designed to have the capability to make subtle PSA cycle parameter changes. Prior art home oxygen concentrators typically utilize a single feed/waste valve assembly that does not allow for independent adjustment of step times. These devices often utilize check valves in place of solenoid valves to control product gas flow, and they use a single fixed orifice to control the purge rate. The PSA cycle steps are all controlled by the single switching of the main feed/waste valve assembly, so the step times and the flow rates are symmetrically fixed for all adsorbent beds in the system. This hardware configuration causes pressure balance asymmetries to be ignored in a stationary concentrator's manufacture and operation.

Industrial scale PSA systems that utilize up to seven large adsorbent beds typically have hardware means to adjust bed parameters individually since the operating cost of an inefficient plant far outweighs the capital cost of adding sensors and controls to the system. The preferred method for balancing PSA bed operation is by monitoring the effluent concentration of the bed during the purge to ensure that the bed is being properly regenerated. While this method enables precise balancing of the bed's oxygen production purity, the equipment required to perform this monitoring would be far too costly and cumbersome to implement in a small portable device. The portable concentrator must be as reliable as the industrial PSA plant even though it does not have an equivalent sensor array or routine maintenance.

In practical use, many things can contribute to symmetry imbalance of the system. In portable lightweight devices, the scale of all parts and adsorbent bed sizes required becomes small, making manufacturing tolerances of parts, such as valves, adsorbent loading (mass or packing factor differences between columns), and assembly critical to proper operation of the PSA cycle. Portable concentrators are also cost sensitive so adding additional sensors or hardware control mechanisms is not advantageous as it is in industrial scale applications. During normal patient use the device will encounter significant levels of shock and vibration which can lead to small leaks in the system that if adjusted for properly could enable the device to continue to operate normally. It is desirable to account for these possibilities in a real-time manner for mass-produced portable devices. The capability to monitor and adjust adsorbent bed pressure accounts for these possibilities, therefore maintaining concentrator reliability and minimizing required maintenance.

BRIEF SUMMARY OF THE INVENTION

In one embodiment of the present invention, a gas concentrator including a compressor, an adsorption section including adsorbent beds, gas flow control valves and a programmable controller is provided. The gas concentrator comprises at least one pressure sensor adapted to monitor adsorbent bed pressure via the output product pressure, and a valve control function that is operatively connected to the programmable controller and adapted to adjust valve operation to achieve balanced pressure in the various adsorbent beds during a peak pressure portion for each bed occurring in an adsorption cycle.

In one version, the pressure is monitored in each bed via a single pressure sensor dedicated to a single bed or a differential pressure sensor across any pair of beds in a multi-bed system. In another version the pressure is monitored in a receiving plenum or product storage vessel as each bed feeds the vessel. In other embodiments, the concentrator may operate using a Pressure Swing Adsorption cycle (PSA), a Vacuum Pressure Swing Adsorption Cycle (VPSA), or strictly using a Vacuum Swing Adsorption Cycle (VSA) where the minimum pressure measurements could be attained via the individual pressure sensor or a common pressure sensor at the vacuum source. In other embodiments, the bed pressure is balanced by adjusting valve timing or flow rate through valves using rate dependent proportional valves.

In another embodiment of the present invention, a method of operating a gas concentrator is provided. The method includes acquiring the peak pressure of each bed during the adsorption cycle via the product output pressure, and adjusting adsorption cycle variables in order to balance the peak product pressure generated by each bed. In one version, each individual bed pressure measurement is acquired. In a preferred embodiment, the pressure is monitored at a plenum or product storage vessel as each bed feeds the vessel.

In one version, bed pressure is balanced by any combination of:

lengthening the feed time for a bed whose pressure is lower, decreasing the purge time for a bed whose pressure is lower, decreasing the feed time for a bed whose pressure is higher, or increasing the purge time for a bed whose pressure is higher.

In a preferred embodiment, the purge and feed time adjustments are accomplished by increasing or decreasing the valve timing associated with the feed and purge valves in unison so that the overall cycle time is not altered, thereby preserving the intended cycle time and zeolite productivity. In another embodiment, the difference between the peak pressure and the pressure after bed blowdown or evacuation is measured, and the valve timing may be adjusted to bring the blowdown or evacuation pressure as low as possible to improve bed regeneration efficiency. This embodiment further ensures that the pressure ratio between the minimum and maximum pressures seen by each bed is substantially equal, regardless of the nominal ambient pressure (such as with a VPSA system).

In one version, the valve timing is accomplished by a program executed by the programmable controller, which acquires the pressure data from pressure sensors and increments or decrements the time periods for opening and closing the feed and purge valves until pressure is balanced among the beds. In other embodiments, the bed pressures are balanced by adjusting the valve flow rates, which also preserves the original cycle time while still achieving proper bed pressure balance.

Another process contemplated is that the programmable controller, upon determining that pressure imbalance is nearing a value which cannot be adjusted for within acceptable bounds within the PSA cycle, generates a service needed message or terminates further adjustments to avoid unacceptable alterations to the PSA cycle.

BRIEF DESCRIPTION OF THE DRAWINGS

The understanding of the following detailed description of the invention will be facilitated by referring to the accompanying figures.

DETAILED DESCRIPTION OF THE INVENTION

Figure 1:
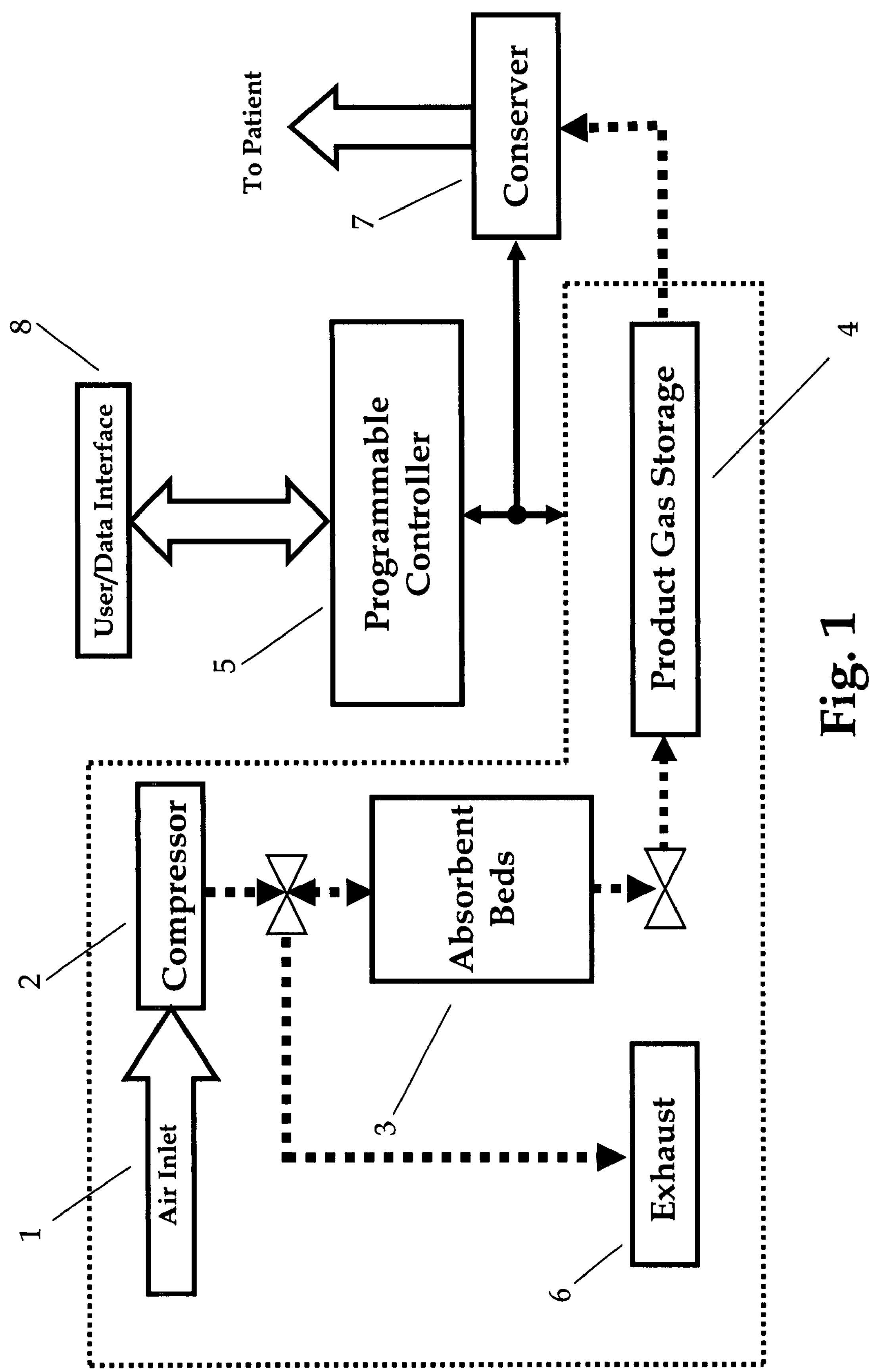
FIG. 1 shows the general elements of gas concentrators as applicable to certain preferred embodiments of the invention.

Referring to FIG. 1, general features of a gas concentrator are shown. Typically gas is drawn into the inlet 1 into a compressor 2. Compressed air is then delivered (through various filters and other devices) to a device for selectively adsorbing a component of the gas. The invention, although applicable to a variety of gas concentrator implementations, will be described in detail for the case where the inlet gas is air, and the adsorber is a PSA adsorber utilizing adsorbent beds 3 which selectively adsorb nitrogen, producing an oxygen rich product gas.

A variety of PSA cycle types and bed arrangements are known in the art, most of which can benefit from the invention. Whatever the details of the adsorber section 3, typically product gas is accumulated in a storage device 4. Storage devices may include a tank in the traditional sense, or may be some other device effective for holding a volume of gas, such as a tube, or some other volume filled with a high surface area-to-volume powder. Many modern concentrators used for therapeutic applications also include a programmable controller 5 to operate the concentrator and provide for user interface and communications 8. Also typical are gas exhaust 6, and delivery to the patient, which often is through a conserver device 7.

Figure 2:
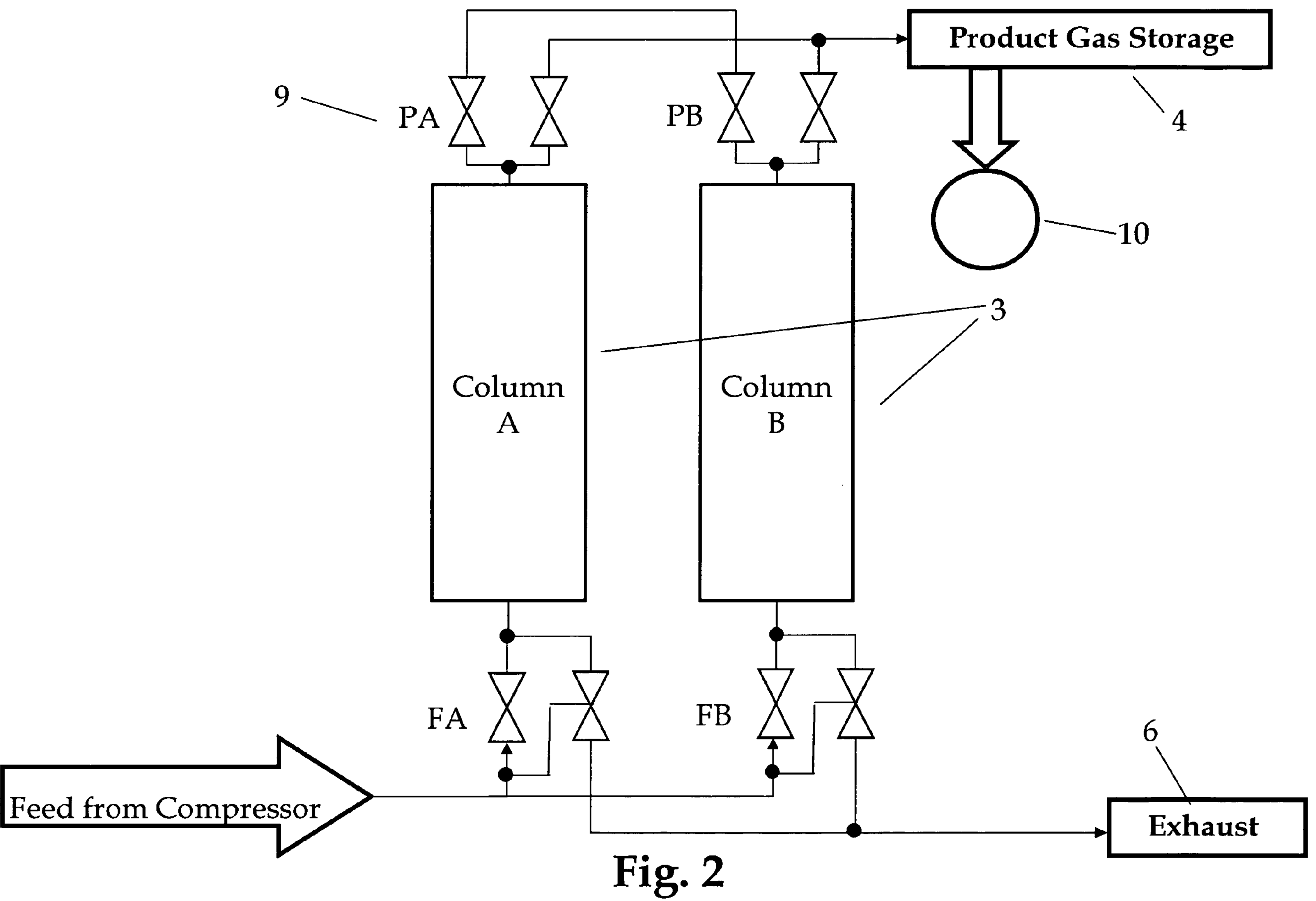
FIG. 2 shows an exemplary arrangement of adsorbent beds and valves which can be used to practice certain preferred embodiments of the invention.

A particular arrangement of a concentrator, illustrating certain preferred embodiments of the invention, is shown in FIG. 2. The arrangement shown is used by way of example because this arrangement allows for practice of many of the invention's advantages. However, other arrangements than the one shown will also benefit from the invention and are within the scope of the invention as claimed.

Referring to FIG. 2, four valves will be discussed. These are the Valves 9 labeled FA, FB, the feed valves for the beds A an B at 3 and PA, PB, the purge valves for beds A and B. Other valves may exist for control of exhaust steps and equalization steps or other functions found in various PSA implementations. However most PSA concentrators have feed and purge control for each bed. Compressed air from the compressor is used to feed the beds, while some concentrated gas siphoned off from lines feeding the product gas storage 4 are used to purge the beds. The purge gas is exhausted at 6. For the operation of certain preferred embodiments of the invention, it is preferable that the timing of the valves operation, or alternately flow through the valves, is controlled by the programmable controller. The concentrator shown in FIG. 2 further includes a gas pressure sensor 10 adapted to monitor pressure in the adsorbent bed. The pressure measurements are preferably used to adjust the valve operation to achieve balanced pressure in the various adsorbent beds. In a preferred embodiment, the gas pressure sensor 10 is adapted to perform other functions, such as compressor feedback control, bolus delivery control, and regulatory compliance. In one preferred embodiment, the pressure sensor 10 already present in the concentrator for regulatory compliance and is adapted to perform the additional function of monitoring the gas pressure for the purpose of balancing the beds. Thus, use of the already available pressure sensor 10, such as a single product line pressure sensor available in a gas concentrator of a preferred embodiment, to balance beds would not impact system cost or complexity, thus producing a significant advantage for portable concentrators compared to the industrial system balancing in the prior art.

Typically in most PSA cycles, the purge and feed steps occur in different beds at different times. In the exemplary two-bed system of FIG. 2, typically one bed is fed while the other is purged. For the operation of certain preferred embodiments of the invention, bed pressure, preferably the peak product output pressure, achieved in each bed at the end of the feed (adsorption) step, is measured. Alternatively, pressure sensors may be present in each bed, but this arrangement has more impact to system design. A minimal impact solution is to use the data already available from the sensor at the product end or in a line connected to each bed, which is preferably interfaced to the programmable controller. Alternatively, a common pressure sensor, interfaced to the controller may be placed in a line leading from the beds to the product gas storage vessel, or within the vessel itself. A pressure sensor measuring the difference in pressure of the two beds from high to low could also be implemented to adapt the invention to work with VPSA or VSA systems without the need for multiple additional pressure sensors. As the controller preferably runs the PSA cycle, it will know when to acquire data from a common pressure sensor corresponding to which points in the cycle corresponds to peak product pressure in each bed or in the product storage vessel.

Figure 3:
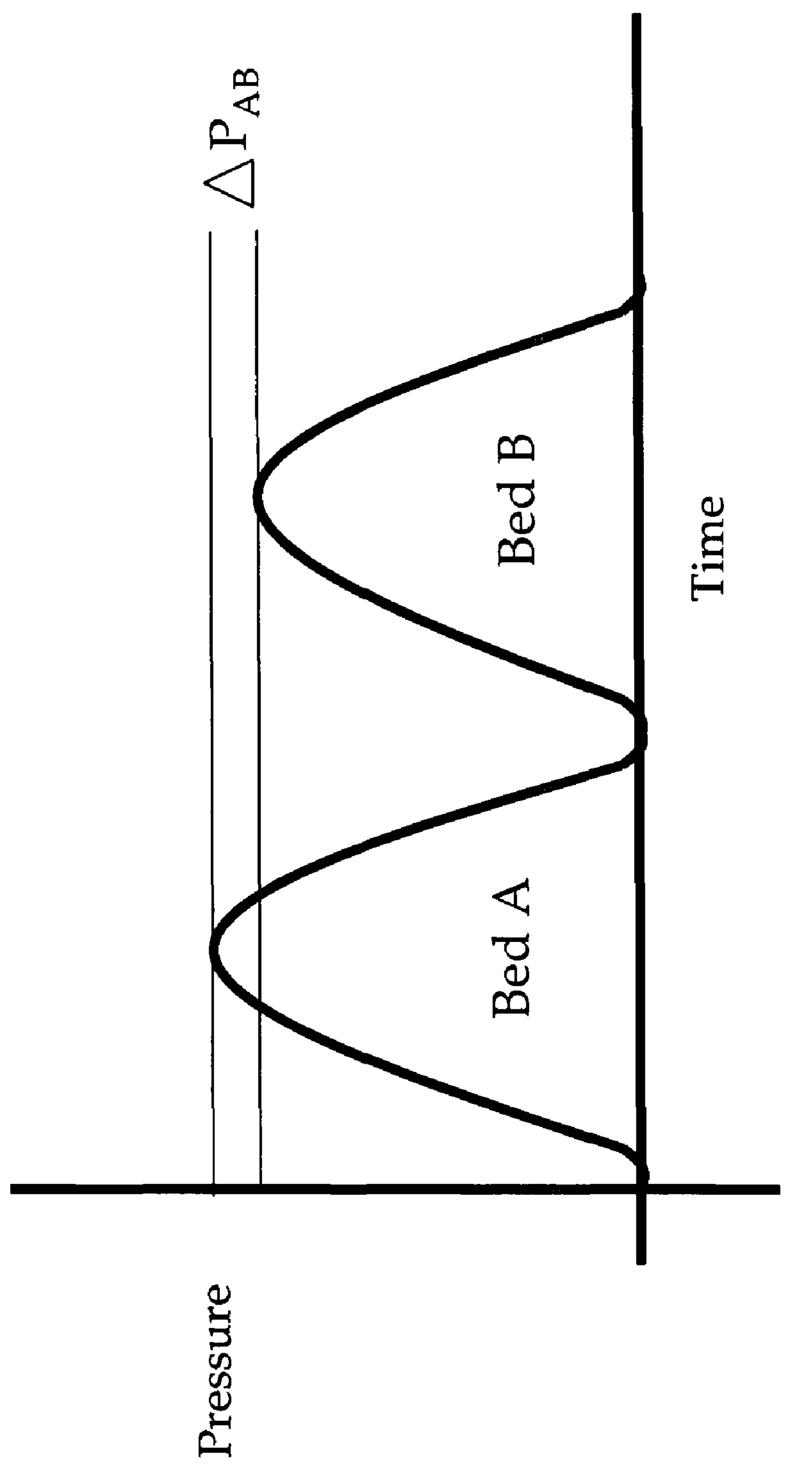
FIG. 3 shows an example of bed pressure imbalance.

Given the ability to measure peak pressure, the operation of the beds may be compared as shown in FIG. 3, a pressure vs. time plot acquired for an exemplary PSA cycle. In the example, the peak pressure in Bed A is higher than the peak pressure in Bed B, indicating that the beds are not balanced. If the beds are out of balance, the efficiency of the concentrator decreases dramatically, leading to lower device performance and reduced manufacturability. With an arrangement as shown in FIG. 2, with independent processor controlled valves, the processor can adjust the valve timing to keep the beds balanced. Conversely, the rate of purge can be adjusted if proportional valves are used in place of solenoid valves, thereby not altering the step times, but achieving the same net change in the volume of purge gas used to regenerate the adsorber.

This ability to detect and fix imbalance has two significant advantages: First it allows for wider tolerances at manufacture, thereby decreasing the cost of the concentrator, and moreover as the concentrator is used in the field as a portable device, aging effects and abuse can cause small leaks, valve perturbations and so on which will cause bed imbalance. The ability to monitor imbalance and make field adjustments can greatly extend the life of the concentrator. Moreover if the imbalance trend is monitored, it may be possible to predict when service is needed before a failure causes the device to stop providing oxygen to a patient.

Figure 4:
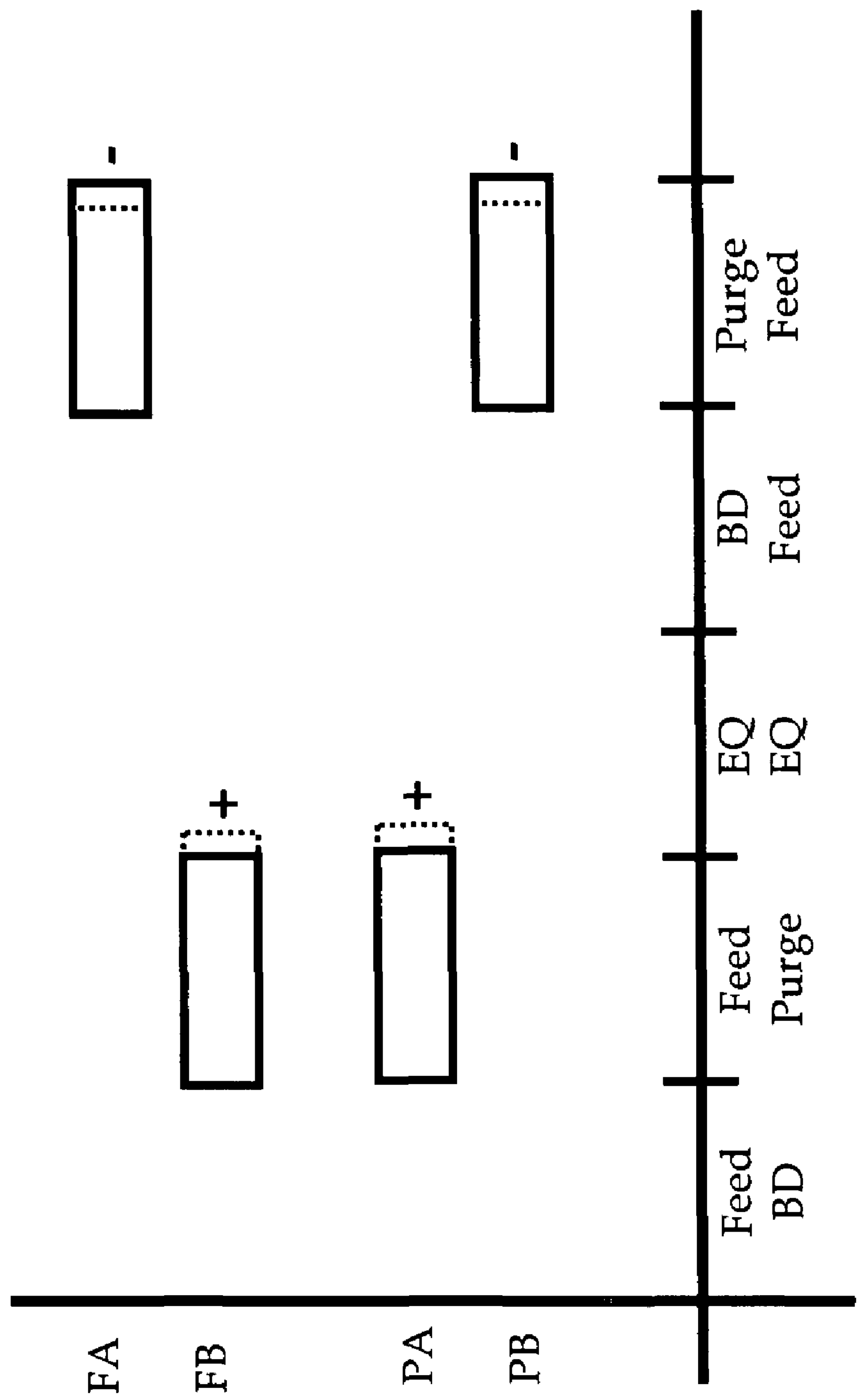
FIG. 4 shows the operation of certain preferred embodiments of the invention to correct for the imbalance.

The operation of the invention is illustrated in FIG. 4 for an exemplary PSA cycle for a two bed, A and B, concentrator. The PSA cycle comprises a series of Feed, Purge, Blow-down (BD) and Equalization (EQ) steps. FIG. 4 shows the valve timing for the four valves, PA, PB, FA, and FB (feed and purge valves for beds A and B). Although the invention may be practiced in many ways, such as, adjusting the equalization times, a preferred embodiment utilizes adjustment of just the feed and purge valve timing, thereby applying to almost any PSA cycle or concentrator/bed arrangement, including systems with more than two beds. Although the example shown uses discreet valves, it would also be possible to advance and/or retard timing steps in systems with one multiport valve for which the switching rate is not binary but rather variable rate where the rotational or linear velocity of the valve is controlled via a microprocessor, such as a rotary or linear plate valve, to achieve similar results.

The default valve timing is indicated in unbroken lines. To adjust for the imbalance shown in FIG. 4, any of the following timing adjustments, shown by dotted lines, may be made. To decrease the peak pressure of A, valve FA on-time (feed time) may be slightly decreased. The peak pressure of A may also be decreased by lengthening valve PA on-time (purge time). B peak pressure may be increased by increasing valve FB on-time. B peak pressure may also be increased by decreasing valve PB on-time. Any one or combination of these adjustments may be used to achieve a balance between the peak product pressure produced by beds A and B, or of any number of beds in almost any PSA system. In the preferred mode of operation, the invention adjusts opposing steps of feed and purge to maintain the original cycle time instead of adding or subtracting time from a single bed to achieve balanced pressure but imbalanced bed cycle times.

Cycle times in portable and home concentrators can range from as little as 4 seconds for rapidly cycling devices to as long as 60 seconds for devices that are turned down far below their maximum capacity. In a portable concentrator, the step times are critical to proper operation and the invention allows for a broad range of adjustments to the step times to ensure precise operation of the PSA cycle. Although there is a practical limit to the adjustment times based on valve response time and the capabilities of the microprocessor, a step time adjustment of as little as 20 milliseconds can improve device performance if the manufacturing tolerances stack-up unfavorably. Conversely, if abuse of the portable concentrator induces a leak in the system, the invention may adjust the cycle times by over 200 milliseconds to counteract the gas lost through the leak.

Of course, bed pressure may be balanced by other means than adjusting valve timing. One possible alternative is to utilize flow rate controllable valves, such as proportional solenoid valves, in the concentrator design. In this embodiment, the feed and purge rates may be adjusted to bring the bed pressures into balance, which would achieve the same net change in the amount of feed gas or purge gas delivered to the adsorber without altering the individual step times. Other possible techniques, within the scope of the invention, will suggest themselves to a skilled practitioner, depending on the parameters under programmable control in a given concentrator design and the array of sensors connected to the microcontroller. Also, the invention applies equally well to other pressure swing regimes, such as VPSA or VSA. The pressure range per se does not form any part of the novelty of the invention.

Figure 5:
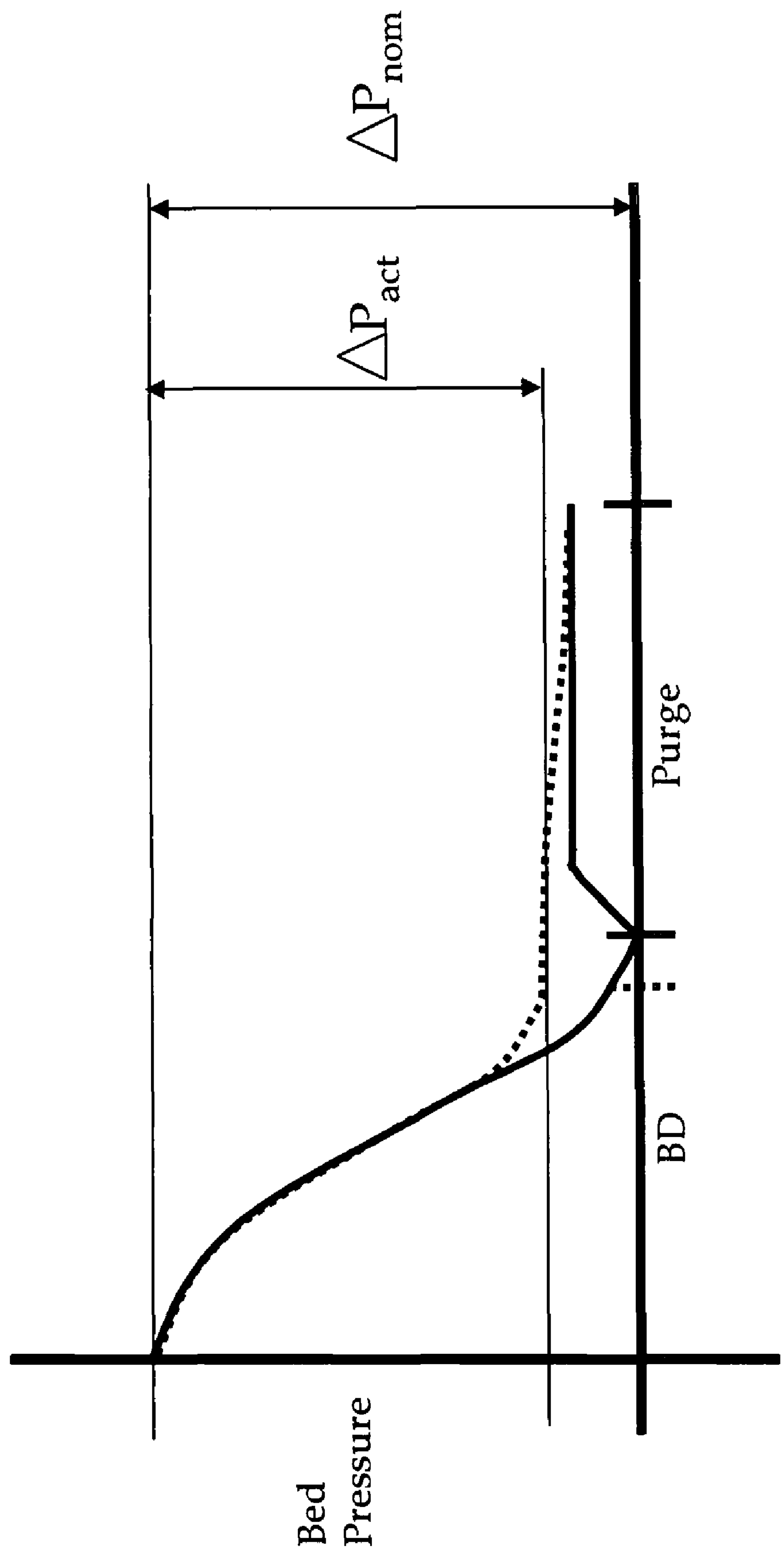
FIG. 5 illustrates information which can be acquired by measuring the minimum bed pressure in addition to the peak pressure.

Depending on the configuration of the concentrator, it may be advantageous to gather data at the low end of the pressure cycle in a concentrator bed. This is more easily accomplished in a system with a pressure sensor dedicated to each bed, and with each pressure sensor placed in a location that experiences the full pressure swing of the corresponding bed. FIG. 5 shows an example of why it may be useful to gather low end pressure measurements. Typically, the pressure builds in a bed during the feed cycle and reaches its maximum at the end of the cycle. When the cycle enters the blow down step (BD), the pressure, as shown, falls to its lowest point. The low point is nominally local ambient atmospheric pressure for a PSA system (but may be a lower pressure for a VPSA system or VSA system), so the difference between peak and lowest pressure is shown as $\Delta P_{nom}$ for normal correct operation. However, if for some reason, the BD cycle time is restricted, or some other defect occurs, the pressure at the end of BD may not reach ambient (or the desired minimum pressure in a VPSA or VSA system). This situation would lead to depressurization continuing during the purge step, which will reduce the efficiency of the regeneration of the adsorbent and require more purge gas to achieve regeneration, thus reducing overall oxygen recovery in the system. This problem can also be corrected by changing valve timing or valve rate (orifice size for flow rate controlling valves).

Thus the preferred embodiments of the invention include the elements of pressure sensor or sensors read by a controller to determine bed peak product pressure, programmable control of bed valve timing, and a controller program to make adjustment of the timing to balance bed pressure. However, just monitoring the bed pressure imbalance is useful in and of itself as an indication of concentrator health and aging.

As can be seen, any home or portable oxygen concentrator design can benefit from the increased information provided by bed pressure balance monitoring. And for concentrators with sufficient valve control and flexibility, adjustments can be made in response to the pressure monitoring information. And as above, the trend can be used to predict service before adjustment mitigation runs out of range. The service indication can be displayed on the user interface or transmitted to a caregiver or service center depending on the design and communication capabilities of the concentrator. Of course, infinite adjustment of valve timing is not possible within the constraints of a given PSA cycle. So a further benefit can be achieved by the controller determining when the range for adjustment is nearing its limit and indicating that service will be needed soon.

We claim:

1. A portable gas concentrator, for therapeutic delivery of oxygen to a patient comprising; a compressor, a controller, a rechargeable power source, an adsorption cycle section including adsorbent beds, at least one purge and/or feed gas flow control valve disposed in each bed and connected to the controller, wherein at least one of valve timing and flow is controlled by the controller, a gas product element a product line disposed to deliver oxygen to a patient, a single pressure sensor connected to the controller and disposed in the gas product element product line; and, a controller configured to read the pressure sensor disposed in the product line and to control oxygen delivery to the patient and to adjust at least one of valve timing and flow to balance peak product gas pressure observed in pressurization cycle steps from data obtained from the pressure sensor disposed in the product line; wherein the portable concentrator is less than 10 lbs, in weight, less than 1 cu. ft. in volume and generates less than 45 dbA acoustic noise.

2. The gas concentrator of claim 1 wherein the adsorption cycle is one of a Pressure Swing Adsorption Cycle (PSA), a Vacuum Pressure Swing Adsorption Cycle (VPSA), or a Vacuum Swing Adsorption Cycle (VSA).

3. The gas concentrator of claim 1 wherein valve timing is adjusted in response to the monitored pressure of the product gas whereby the bed pressures are balanced without affecting the overall cycle time.

* * * * *